United States Patent [19]

Loeb et al.

[11] 4,072,574

[45] Feb. 7, 1978

[54] SYSTEM FOR IN VITRO ASSAY FOR MUTAGENICITY AND/OR CARCINOGENICITY OF CHEMICALS OR OTHER EXOGENOUS AGENTS

[75] Inventors: Lawrence A. Loeb, Elkins Park; Michael A. Sirover, Philadelphia, both of Pa.

[73] Assignee: The Institute for Cancer Research, Fox Chase, Pa.

[21] Appl. No.: 710,314

[22] Filed: July 30, 1976

[51] Int. Cl.$^2$ ................................................ C12K 1/00
[52] U.S. Cl. ............................ 195/103.5 R; 195/28 N
[58] Field of Search ........................ 195/103.5 R, 28 N

[56] References Cited

U.S. PATENT DOCUMENTS 3,816,263  6/1974  Rabin et al. ................... 195/103.5 R
3,850,749  11/1974  Kaufmann et al. ................ 195/28 N

*Primary Examiner*—Alvin E. Tanenholtz
*Attorney, Agent, or Firm*—Jackson, Jackson & Chovanes

[57] ABSTRACT

This involves an in vitro assay system to screen for mutagenic and/or carcinogenic agents based on alterations in the fidelity of DNA synthesis. In the system, chemicals will be tested for their mutagenicity or carcinogenicity by measuring increases in the number of mistakes incorporated by purified DNA polymerases using synthetic polynucleotide templates. This system offers the advantage of performing this analysis in the test tube so that all parameters in the reaction can be monitored. Agents that enhance misincorporation during DNA synthesis would be predicted to have a higher probability of being mutagens or carcinogens in the human population.

9 Claims, No Drawings

SYSTEM FOR IN VITRO ASSAY FOR MUTAGENICITY AND/OR CARCINOGENICITY OF CHEMICALS OR OTHER EXOGENOUS AGENTS

INTRODUCTORY DESCRIPTION

This invention relates to a system for the in vitro screening for potential mutagenicity and/or carcinogenicity of chemicals or other exogenous agents.

A purpose of this invention is to provide a means of screening for the likelihood of mutagenicity or carcinogenicity of substances which is comparatively easy and inexpensive to perform.

A further purpose is to provide such a means in which all parameters in the reaction can be monitored.

A further purpose is to provide such a means which does not require the use of living organisms.

A further purpose is to provide such a means which has an especially broad range of substances to which it is applicable.

RATIONALE

It has been estimated that approximately 50,000 new chemicals are introduced yearly into our environment in the United States. Moreover, mixtures of these chemicals may have greater carcinogenic properties than the isolated components themselves. Although the toxic properties of many of these agents can be quantitated in a variety of test systems, the mutagenic and/or carcinogenetic potentials of these chemicals have been extremely difficult to ascertain. In the past it has only been by hindsight that the carcinogenicity or mutagenicity of a variety of industrial chemicalbecame known. For the most part identification of chemical carcinogens has been restricted to uique industrial occupations or to a localized geographical distribution. This is illustrated by the increased incidence of nasal and lung tumors in workers in the nickel industry, by the increased incidence of tumors in workers exposed to polyvinyl chloride, and by the increased incidence of uterine tumors in the female progeny of women who had taken diethylstilbesterol during pregnancy.

Even these retrospective studies are hampered by the difficulties in quantitating the amount of carcinogens in the environment, by the infrequency of certain malignancies, and by the exceptionally long latent period between an exposure to a carcinogen and the onset of malignancy. For these reasons considerable effort has been directed to develop systems for the rapid, efficient assay of potential human mutagens and carcinogens. Until recently, the determination of mutagenicity or carcinogenicity of a particular agent depended solely on in vivo animal experimentation. Unfortunately, in order to test any agent adequately, these experiments require maintenance of large numbers of animals for long periods of time so that an analysis of each chemical may cost a great deal of money, such as for example on the order of two hundred thousand dollars, and may require several years. Thus, the general population would be exposed to this compound for the duration of the test or the use of the compound would be delayed several years. It will be evident that this method is not applicable for determining the carcinogenicity or mutagenicity of a vast number of agents or mixtures of agents. It will be necessary to use short-term inexpensive in vitro detection techniques to initially screen the vast majority of compounds. In this manner subsequent animal studies can be focused carefully on targeted compounds. This application involves an in vitro system which might help in pre-screening a number of these compounds.

Current Methods for Pre-screening for Chemical Carcinogens

There are two current groups of cell mediated assay systems which are being used to determine the potential mutagenicity and/or carcinogenicity of exogenous agents. The first and by far the most widely used system involves the use of special tester bacterial strains. This system tests for mutagenicity by measuring the ability of compounds to revert previously induced mutations in a bacterium. This system of analysis is best exemplified by the so-called Ames test, in which the mutational effects of particular agents are determined by their ability to revert specific mutations in Salmonella typhimurium. This system has been shown to have an exceptionally high predictive value for known chemical carcinogens. This system has been extended by using microsomal enzymes from rat liver that can activate particular agents so that they become mutagenic or/carcinogenic. Unfortunately, this system has failed to detect carcinogenic metal compounds and several other types of substances. So far, all carcinogenic metal compounds which have been tested in this system have been scored as negative.

The second group of such systems involves the measurement of transformation rates or the induction of varients (different cells) in animal cell cultures. These measurements are usually carried out in Chinese hamster cells in culture to detect cell variants or in virus-infected fibroblast cultures to measure virus induction. It is the latter system that may be applicable to testing metal carcinogens. These two systems have the advantage of using animal cells as a measure of mutagenicity or carcinogenicity. However, they are much more time consuming and expensive than the bacterial systems.

The system of the present invention is intended to be a rapid and efficient in vitro biochemical assay to screen chemicals for their mutagenicity and/or carcinogenicity. The test will not involve bacteria or animal cells in culture. The tests should be able to be performed in a routine chemical laboratory by technicians under the guidance of professional staff. In this sytem we will measure the accuracy by which DNA polymerases copy polynucleotides of known composition in the presence of suspected carcinogens and mutagens.

It is expected that substances which exhibit a relatively substantial likelihood of mutagenicity or carcinogenicity will be evaluated further by some other means if their likelihood of use would make any such mutagenicity or carcinogenicity a matter of concern under the circumstances.

The proposed screening method provides for the rapid test of an exogenous agent. It may be possible that the tests of a specific compound may be completed within one week. At that time the results could be sufficient to designate the said compound as positive or negative in the test. We envision that this test system will be used along with the current methods using bacterial and cell culture. By a combination of these methods, rational choices may be made for the introduction of compounds into the environment, and for further testing in animal systems.

· Deduction for Practice in the Laboratory

In this invention, the ability of carcinogens to decrease the fidelity of in vitro DNA synthesis will be used to screen for carcinogenic or mutagenic agents. The system uses synthetic polynucleotides of defined composition which may be copied in the test tubes with procaryotic, eucaryotic or viral DNA polymerases. The use of synthetic polynucleotides of defined composition allows the measurement of the simultaneous incorporation of the correct, complementary nucleotide and an incorrect, non-complementary nucleotide. The correct nucleotide is labeled with [$\alpha$-$^{32}$P] of low specific activity and the incorrect nucleotide is labeled with [$^3$H] of high specific activity. Through this double labeled reaction it is possible to determine the simultaneous incorporation of both nucleotides and thus to determine an error frequency. The error frequency may be defined as the ratio of the incorrect/correct nucleotide incorporation. Agents which increase this error frequency may be scored as positive. Agents which do not influence the error frequency could be scored as negative. Agents which score positive would be checked using different templates to underscore the positive results. In this system different polymerases will be used as well as different templates. One would expect that most carcinogens would change the fidelity of DNA synthesis with different polymerases as well as with different templates though this need not be the case. A combination of these systems will increase the accuracy of this system by preventing false positives or negatives in the tests.

It is anticipated that it will be necessary in some instances to use eucaryotic microsomal activating enzymes to metabolize the proximate carcinogen to the ultimate carcinogen. Methods for using activating enzymes from rat liver have been worked out by Ames in the bacterial system. Similar methods are intended to be applied to this in vitro system.

EXAMPLES

Each assay will consist of a polymerase, a polynucleotide template that only contains one or two nucleotides, a complementary nucleotide and a non-complementary nucleotide as well as magnesium. Both of the nucleotides will be labeled by radioactive precursors and the ratio between the two is to be used for a measure of error frequency in the system. In instances where a template requires two complementary nucleotides, only one will be radioactively labeled.

We have used the system in the laboratory for studying the fidelity of DNA synthesis as indicated in the accompanying references. Initial experiments have been performed to determine the utility of this system with poly (rA).oligo ($d$T), poly [d(A-T)], and poly (rC).oligo ($d$G) as templates and avian myeloblastosis virus DNA polymerase. The feasibility of this test system has been established, not only this polymerase will be used, but also bacterial DNA polymerases as well as polymerases purified from animal and human cells.

We have been able to demonstrate that beryllium, a carcinogenic metal which induces pulmonary carcinomas in monkey and osteogenic sarcomas in rabbits, alters the fidelity of DNA synthesis in this system. The addition of beryllium (BeCl$_2$) to this system decreases the fidelity by which AMV DNA polymerase copies these templates.

$\beta$-propiolactone is a carcinogen in mice, rats and hamsters. It is one of 15 carcinogens officially listed by the U.S. government as possibly being carcinogenic in humans. The addition of $\beta$-propiolactone to this system decreases the fidelity by which AMV DNA polymerase and sea urchin nuclear DNA polymerase copy poly ($d$A).oligo ($d$T) as a template.

Certain other metal carcinogens, and more particularly, cobalt, nickel and manganese, have each been found to alter the fidelity by which AMV DNA polymerase copies a variety of templates. The results of a triple-blind study on the ability of metals to alter the fidelity of DNA synthesis are found in Table 1 and some details are given in Table 2.

A large number of non-carcinogenic compounds have been added to this system and have been shown not to alter the fidelity of DNA synthesis.

The addition of a number of toxic agents which stop the polymerase from working in this system does not alter the fidelity of DNA synthesis.

The foregoing are examples of use of the system as it would be used as an initial screen for mutagens or carcinogens.

Materials.

Unlabeled deoxynucleotides, Tritiumlabeled nucleotides, and $_{32}$P labeled nucleotides are known materials which can be purchased from commercial suppliers.

Poly [d(A-T)] was prepared by a de novo catalyzed reaction using *E. coli* DNA polymerase I (11). It and all other synthetic polynucleotide templates are known materials which can be purchased from commercial suppliers.

Purification of Avian Myeloblastosis Virus DNA Polymerase.

Avian myeloblastosis virus was separated from the plasma of infected chickens by velocity and equilibrium centrifugations. The virions were disrupted by the method of Kacian and Spiegelman and the polymerase was purified by chromatography on DEAE-cellulose and on phosphocellulose according to the procedure of Hurwitz and Leis.

DNA Polymerase Assay

Reactions (total volume 0.05 ml) which measured complementary nucleotide incorporation contained 50 mM Tris-HCL (pH 8.0), 20 mM KCl, 5 mM dithiothreitol, 5 mM MgCl$_2$, 2$\mu$g BSA, 25 M [$\alpha$-$^{32}$P] -dTTP (60 dpm/pmole), 1$\mu$g poly (A).oligo (dT) (1:1.5 mass ratio), and 0.45 $\mu$g of AMV DNA polymerase. For simultaneous quantitation of complementary and non-complementary nucleotide incorporation each reaction was modified to contain 26$\mu$M [$\alpha$-$^{32}$P]dTTP (12 dpm/pmole) and 23$\mu$M [$^3$H]-dCTP (50,000 dpm/pmole). With 1$\mu$g of poly (C).oligo ($d$G) as a template the reaction mixture contained 25 mM Tris-HCl (pH 810), 10 mM KCl, 3 mM MgCl$_2$, 3 mM dithiothreitol, 20 M [$\alpha$-$^{32}$P]-dGTP (4 dpm/pmole), 19.2 $\mu$M [$^3$H]-dATP (20,000 dpm/pmole), and 0.45 $\mu$g of AMV DNA polymerase. Metals were added directly to the reaction mixture as aqueous solutions of chloride salts. All reactions were incubated for 60 min. at 37° C. Incorporation of radioactive nucleotides into an acid-insoluble and alkali-resistant product was determined by using the precipitation-solubilization procedure as described by Battula and Loeb. All experiments were performed in triplicate and the averages were determined. All experiments were repeated several times and incorporation of the non-complementary deoxynucleotide was at least twice the zero time incorporation in each experiment.

RESULTS

Metal Requirements for Catalysis by AMV DNA Polymerase

All known DNA polymerases require either $Mg^{2+}$ or $Mn^{2+}$ as an added divalent cation for activity. AMV DNA polymerase used $Mg^{2+}$ as an added divalent cation and the maximum rate of polymerization with poly (A).oligo (dT) was attained at 5 mM $Mg^{2+}$. In the absence of $Mg^{2+}$, the addition of $Be^{2+}$ in concentrations as great as 15 mM did not result in detectable poly (dT) synthesis. Thymidine monophosphate incorporation with $Be^{2+}$ was less than 0.3% of that obtained with 5 mM $Mg^{2+}$. Similarly, the divalent cations $Ca^{2+}$ and $Ba^{2+}$ were unable to substitute for $Mg^{2+}$. However, preliminary results suggest that $Co^{2+}$ and $Ni^{2+}$ serve as metal activators with several DNA polymerases.

Influence of Metals on Fidelity

In order to determine the effect of different metals on the accuracy of DNA replication, metal cations were added as chloride salts directly to the polymerase reaction. In these experiments, poly (A).oligo (dT) was the template-primer and the simultaneous incorporation of complementary nucleotide, $[\alpha-^{32}P]$-dTMP, and the non-complementery nucleotide, $[^3H]$-dCMP, was determined. The error frequency, i.e., the ratio of non-complementary to complementary nucleotide incorporated, was invariant with respect to $Mg^{2+}$ concentration (Table 3). Only upon the addition of $Be^{2+}$ was the error frequency increased. In this experiment, AMV DNA polymerase incorporated one non-complementary nucleotide for every 1128 complementary nucleotides polymerized with 5 mM $Mg^{2+}$. The addition of graded amounts of $Be^{2+}$ resulted in a nearly proportional increase in the frequency of dCMP incorporation. With 10 mM $Be^{2+}$ the error frequency was increased 15 fold to 1/75. The addition of $Ca^{2+}$ inhibited in parallel the incorporation of the complementary and non-complementary nucleotide and thus did not alter the error frequency. The addition of $Ba^{2+}$ or $Sr^{2+}$ did not affect either the incorporation of the complementary or non-complementary nucleotides. Similarly, a variety of chemicals lacking known carcinogenic or mutagenic activity did not alter the fidelity of DNA synthesis in this system. These include spermidine (0.1 to 5 mM), KCl (1 mM to 300 mM), alteration in pH (6.0 to 8.5), caffeine (0.1–20 mM) and retinol (0.2–2μg). The increased error frequency induced by $Be^{2+}$ was not limited to poly (A).oligo (dT) as the template nor to dCTP as the non-complementary nucleotide (Table II) suggesting that the interaction of $Be^{2+}$ is with the polymerase itself.

In the tests, it is likely to be advisable to run the particular test in duplicate or triplicate at different concentrations of the substance being tested, as far as that part of the test which incorporates that substance is concerned. This can be compared with the control, which should be run more than once, preferably in triplicate.

A particular non-limiting example of use of the system is one in which fidelity of DNA synthesis is determined in a reaction (total volume 0.05 ml) which contains:

1. 100 mM Tris-maleate (pH 7.6). 2. 60 mM potassium chloride.
3. 5 mM magnesium chloride.
4. Polynucleotide template.
5. Complementary nucleotide labeled with $[\alpha-^{32}P]$.
6. Non-complementary nucleotide (labeled with $[^3H]$.
7. DNA polymerase.

Items 1–3 are standard biochemical reagents. In the last four items, the exact amounts depend upon the particular items being used.

As indicated, in part of tests a test compound will be added as for example various concentrations of beryllium chloride (0.1 through 10 mM).

For example with poly [d(A-T)] as a template and avian myeloblastosis virus (AMV) DMA polymerase, the assay would include items 1–3 plus:

4. 1 μg poly [d(A-T)].
5. 50 μM dATP.
6. 50 μM $[^3H]$ dTTP (5–20 dpm/pmole).
7. 50 μM $[^3H]$ dGTP (10,000–50,000 dpm/pmole).
8. 0.5 μg AMV DNA polymerase.

The same process and test system substituting however an RNA polymerase and its appropriate substrates, including especially appropriate nucleotides, can be also used, performing the assay as an RNA sythesis. This would involve a polynucleotide template.

Where the template is a polydeoxynucleotide template, as in the specific example above given involving avian myeloblastosis virus, to mention only one example, this template can also if desired be copied by an RNA polymerase, to produce RNA, rather than as indicated in the ordinary case in at least most of the preceding, copying it by a DNA polymerase.

In view of our invention and disclosure, variations and modifications to meet individual whim or particular need will doubtless become evident to others skilled in the art to obtain all or part of the benefits of our invention without copying the method and composition shown, and we, therefore, claim all such insofar as they fall within the reasonable spirit and scope of our claims.

Table 1

Effect of Metal Compounds on the Fidelity of DNA Synthesis

| Compound | Class | Template | Δ Error Frequency: (Metal Concentration-mM) | Decreased Fidelity | Carcinogen or Mutagen |
|---|---|---|---|---|---|
| *(Al)$_2$(SO$_4$)$_3$ | 2 | [d(A-T)] | 0.99 (10) | — | — |
| *AgNO$_3$ | 1 | [d(A-T)] | 1.85 (0.03) | + | + |
| *Ba(C$_2$H$_3$O$_2$)$_2$ | 2 | [d(A-T)] | 0.94 (10) | — | — |
| BaCl$_2$ | 2 | poly (A) | 1.17 (10) | — | — |
| BeCl$_2$ | 1 | poly (A) | 15 (10) | + | + |
| CaCl$_2$ | 2 | poly (A) | 1.28 (5) | — | — |
| *Cd(C$_2$H$_3$O$_2$)$_2$ | 1 | poly (C) | 2.22 (0.24) | + | + |
| *CdCl$_2$ | 1 | poly (C) | 1.35 (0.04) | + | + |
| CoCl$_2$ | 1 | poly (C) | 8.37 (4) | + | + |
| *CrCl$_2$ | 1 | [d(A-T)] | 3.70 (0.64) | + | + |
| *CrO$_3$ | 1 | [d(A-T)] | 3.83 (16) | + | + |
| *Cu(C$_2$H$_3$O$_2$)$_2$ | 1 | poly (C) | 1.83 (0.12) | + | ± |
| *CuCl$_2$ | 1 | poly (C) | 2.90 (0.08) | + | ± |

Table 1-continued
Effect of Metal Compounds on the Fidelity of DNA Synthesis

| Compound | Class | Template | Δ Error Frequency: (Metal Concentration-mM) | Decreased Fidelity | Carcinogen or Mutagen |
|---|---|---|---|---|---|
| *$FeCl_2$ | 2 | poly (C) | 1.14 (4) | − | ± |
| *$KC_2H_3O_2$ | 3 | poly (C) | 0.98 (100) | − | − |
| *KCl | 2 | [d(A-T)] | 1.11 (150) | − | − |
| *$K_2HPO_4$ | 2 | [d(A-T)] | 0.74 (40) | − | − |
| *$KH_2PO_4$ | 2 | [d(A-T)] | 1.05 (80) | − | − |
| *$MgSO_4$ | 3 | poly (C) | 1.11 (10) | − | − |
| $MnCl_2$ | 1 | poly (C) | 3.75 (10) | + | + |
| *$NaC_2H_3O_2$ | 2 | poly (C) | 1.00 (100) | − | − |
| *NaCl | 2 | [d(A-T)] | 0.81 (120) | − | − |
| *$NaHCO_3$ | 2 | [d(A-T)] | 0.96 (40) | − | − |
| *NaOH | 3 | [d(A-T)] | 1.17 (10) | − | − |
| *$NH_4COOH$ | 2 | [d(A-T)] | 0.83 (100) | − | − |
| $(NH_4)_2SO_4$ | 2 | poly (C) | 0.94 (120) | − | − |
| $NiCl_2$ | 1 | poly (C) | 1.92 (8) | + | + |
| *$PbCl_2$ | 1 | poly (C) | 1.48 (4) | + | + |
| *$RbCl_2$ | 2 | [d(A-T)] | 0.90 (20) | − | − |
| $SrCl_2$ | 3 | poly (A) | 0.86 (10) | − | − |
| *$ZnCl_2$ | 2 | [d(A-T)] | 1.06 (0.4) | − | ± |

The effect of metal salts on the fidelity of DNA synthesis was examined by testing each of the metal salts at a minimum of seven different concentrations. Compounds were scored as positive if during this titration the error frequency was increased by greater than 30% at two or more concentrations. Compound were scored as negative if they did not fulfill these criteria. The fidelity of DNA synthesis using poly [d(A-T)] as the template was measured in a reaction (total volume 0.05 ml) which contained 100 mM Tris-maleate (pH 7.6); 60 mM KCl; 5 mM $MgCl_2$; 50 μM dATP; 50 μM [α-$^{32}$P]dTTP (5-20 dpm/pmole); 50 μM [$^3$H]dGTP or [$^3$H]dCTP (10,000-50,000 dpm/pmole); 1 μg poly [d(A-T)] and 0.5 μg AMV DNA polymerase. For reactions which used poly (C).oligo (dG) as the template, the incubation mixtures were altered to include 3 mM $MgCl_2$; 10 mM DCl; 20 μM [α-$^{32}$P]dGTP (5-20 dpm/pmole) and 20 μM [$^3$H]dATP (10,000–50,000 dpm/pmole). For reactions which used poly (A)-oligo(dT) as the template, the incubation mixtures were altered to include 50 mM Tris-HCl (pH 8.0); 5 mM $MgCl_2$; 20 mM KCl, 5 mM dithiothreitol; 2 μg BSA, 26 μM [α-$^{32}$P]dTTP (12 dpm/pmole) and 23 μM [$^3$H]dCTP (50,000 dpm/pmole). All reaction mixtures were incubated for 60 min. at 37°. Incorporation of the radioactive deoxynucleotides into an acid insoluble precipitate was determined after repeatedly precipitating the polynucleotide product with 1.0 N perchloric acid and solubilizing with 0.2 M NaOH. All assays were performed in duplicate and the averages determined. Error frequencies were calculated only when the incorporation of the radioactive deoxynucleotides was at least two times the zero time controls. The maximum change in error frequency was calculated by dividing the highest error frequency during the titration by the error frequency determined without the added metal within the same experiment. The metal concentration in parenthesis is that which yielded the largest observed change in error rate. All metal salts assayed in the triple blind experiments were designated as carcinogens, marginal carcinogens, or non-carcinogenic prior to their identification. *Compounds tested in the triple blind experiments.

Table 2
Characterization of Compounds Added to Fidelity Reaction

| Class | Metal | mM | Template/Non-Complementary Deoxynucleotide | Complementary Deoxynucleotide Incorporation (pmoles) | Non-complementary Deoxynucleotide Incorporation (pmoles) | Error Frequency |
|---|---|---|---|---|---|---|
| 1 | $CrCl_2$ | 0 | poly[d(A-T)] / dCTP | 192 | 0.27 | 1/711 |
| | | 0.08 | | 133 | 0.23 | 1/578 |
| | | 0.16 | | 169 | 0.32 | 1/528 |
| | | 0.24 | | 127 | 0.35 | 1/363 |
| | | 0.64 | | 71 | 0.37 | 1/192 |
| | $CuCl_2$ | 0 | poly (C) / dATP | 565 | 0.68 | 1/831 |
| | | 0.02 | | 385 | 0.44 | 1/875 |
| | | 0.04 | | 130 | 0.18 | 1/722 |
| | | 0.08 | | 54 | 0.10 | 1/540 |
| | | 0.12 | | 36 | 0.08 | 1/450 |
| 2 | $Ca(C_2H_3O_2)_2$ | 0 | poly[d(A-T)] / dCTP | 225 | 0.23 | 1/978 |
| | | 0.8 | | 217 | 0.22 | 1/986 |
| | | 2.4 | | 78 | 0.08 | 1/975 |
| | | 4.0 | | 39 | 0.04 | 1/975 |
| | | 4.8 | | 17 | 0.02 | 1/850 |
| | $K_2HPO_4$ | 0 | poly[d(A-T)] / dCTP | 192 | 0.27 | 1/711 |
| | | 8 | | 179 | 0.22 | 1/814 |
| | | 16 | | 180 | 0.23 | 1/783 |
| | | 32 | | 107 | 0.13 | 1/823 |
| | | 40 | | 48 | 0.05 | 1/960 |

Table 2-continued

Characterization of Compounds Added to Fidelity Reaction

| Class | Metal | mM | Template/Non-Complementary Deoxynucleotide | Complementary Deoxynucleotide Incorporation (pmoles) | Non-complementary Deoxynucleotide Incorporation (pmoles) | Error Frequency |
|---|---|---|---|---|---|---|
|   |   | 0 |   | 480 | 0.65 | 1/738 |
|   |   | 4 |   | 484 | 0.66 | 1/733 |
|   | $KC_2H_3O_2$ | 20 | poly (C) / dATP | 423 | 0.56 | 1/755 |
|   |   | 40 |   | 378 | 0.51 | 1/741 |
|   |   | 80 |   | 379 | 0.51 | 1/743 |
| 3 |   |   |   |   |   |   |
|   |   | 0 |   | 303 | 0.44 | 1/689 |
|   |   | 4 |   | 299 | 0.50 | 1/598 |
|   | $MgSO_4$ | 6 | poly (C) / dATP | 398 | 0.63 | 1/632 |
|   |   | 8 |   | 349 | 0.55 | 1/635 |
|   |   | 10 |   | 360 | 0.58 | 1/621 |

All reactions were performed as described in the legend to Table 1. Error frequencies were calculated as single base substitutions.

Table 3

Effects of Divalent Cations on Complementary and Non-Complementary Nucleotide Incorporation

| Divalent Cations | Complementary Nucleotide (pmoles dTMP) | Non-Complementary Nucleotide (pmoles dCMP) | Error Frequency |
|---|---|---|---|
| $Mg^{2+}$ (2 mM) | 320 | 0.56 | 1/571 |
| (5 mM) | 600 | 1.16 | 1/517 |
| (8 mM) | 520 | 1.00 | 1/520 |
| (15 mM) | 240 | 0.90 | 1/600 |
| $Mg^{2+}$ (5 mM) | 990 | 0.878 | 1/1128 |
| " + $Be^{2+}$ ( 2 mM) | 291 | 0.372 | 1/782 |
| " + $Be^{2+}$ ( 5 mM) | 133 | 0.294 | 1/453 |
| " + $Be^{2+}$ (10 mM) | 8.6 | 0.114 | 1/75 |
| $Mg^{2+}$ (5 mM) | 839 | 0.99 | 1/848 |
| " + $Ca^{2+}$ ( 1 mM) | 704 | 0.70 | 1/1005 |
| " + $Ca^{2+}$ ( 2 mM) | 129 | 0.19 | 1/681 |
| " + $Ca^{2+}$ ( 5 mM) | 55 | 0.083 | 1/665 |
| $Mg^{2+}$ (5 mM) | 839 | 0.99 | 1/848 |
| " + $Sr^{2+}$ ( 4 mM) | 798 | 0.86 | 1/927 |
| " + $Sr^{2+}$ ( 6 mM) | 936 | 0.96 | 1/975 |
| " + $Sr^{2+}$ (10 mM) | 845 | 0.86 | 1/982 |
| $Mg^{2+}$ (5 mM) | 232 | 0.38 | 1/610 |
| " + $Ba^{2+}$ ( 2 mM) | 240 | 0.42 | 1/578 |
| " + $Ba^{2+}$ ( 6 mM) | 243 | 0.46 | 1/528 |
| " + $Ba^{2+}$ (10 mM) | 317 | 0.61 | 1/520 |

The frequency of non-complementary nucleotides incorporation was determined as described in "Methods".

Table 4

Effect of $Be^{2+}$ on Catalysis with Different Template-Primers

| Template-primer | Non-Complementary Nucleotide | Beryllium Chloride (mM) | Complementary Nucleotide Incorporation (pmole) | Non-Complementary Nucleotide Incorporation (pmole) | Error Frequency |
|---|---|---|---|---|---|
| poly (C) . oligo (dG) | dATP | 0 | 520 | 0.270 | 1/1925 |
|   |   | 1 | 181 | 0.110 | 1/1649 |
|   |   | 2 | 81 | 0.079 | 1/1025 |
|   |   | 4 | 57 | 0.062 | 1/919 |
|   |   | 5 | 64 | 0.077 | 1/831 |
| poly d(A-T) | dCTP | 0 | 337 | 0.240 | 1/1402 |
|   |   | 1 | 209 | 0.160 | 1/1306 |
|   |   | 3 | 137 | 0.140 | 1/979 |
|   |   | 5 | 97 | 0.140 | 1/689 |
| poly (A) . oligo (dT) | rGTP | 0 | 610 | 0.074 | 1/8245 |
|   |   | 1 | 568 | 0.093 | 1/6104 |
|   |   | 2 | 503 | 0.186 | 1/2704 |
|   |   | 5 | 128 | 0.263 | 1/487 |
|   |   | 10 | 52 | 0.349 | 1/149 |

Reaction conditions for poly (A) . oligo (dT) and poly (C) . oligo (dG) are described in "Methods". Error analysis using poly [d(A-T)] was determined in a reaction mixture (total volume 0.05 ml) which contained 50 mM Tris-HCl (pH 8.0), 20 mM KCl, 4 mM dithiothreitol, 5 mM $MgCl_2$, 1 μg BSA, 100 μM dATP, 100 μM [α-$^{32}$P]-dTTP (4 dpm/pmole), 100 μM [$^3$H]dCTP (25,000 dpm/pmole), 1 μg poly [d(A-T)] and 0.45 μg AMV DNA polymerase. Reaction mixtures were incubated at 37° C for 60 minutes.

Having thus described our invention what we claim as new and desire to secure by Letters Patent is:

1. The method of testing in vitro for the likelihood of mutagenic or carcinogenic properties in a given substance which comprises copying polynucleotides of known composition in the presence of the substance by means of DNA polymerases in a solution which also contains correct complementary nucleotides for said polynucleotides and non-complementary nucleotides for said polynucleotides, and also doing the same incorrect copying in the absence of the substance, and measuring the relative accuracy of the respective copying.

2. The method of testing a substance for the likelihood of mutagenic or carcinogenic properties which comprises replicating a polynucleotide by having a DNA polymerase copy a polynucleotide of known composition in the absence of the substance in a solution including both a correct complementary and an incorrect non-complementary nucleotide for said polynucleotide, also replicating the same polynucleotide by having the same polymerase copy said polynucleotide in the presence of that substance in a solution including the same correct and incorrect nucleotides for said polynucleotides and comparing the results from the standpoint of producing mutations.

3. The method of testing for the likelihood of mutagenic or carcinogenic properties which comprises including in a solution of a polynucleotide, a nucleotide which is a correct nucleotide for that particular polynucleotide, a nucleotide which is not a correct nucleotide for that particular polynucleotide and a polymerase; replicating the polynucleotide in said solution in which a substance to be tested for its likelihood of mutagenic or carcinogenic properties is also included also replicating the polynucleotide in an identical solution in which said substance to be tested is not included and comparing the results from the standpoint of producing mutations.

4. The method of claim 3, in which $Mg^{2+}$ is also included in the solution.

5. The method of claim 3, in which there is used a synthetic polynucleotide of defined composition which may be copied with procaryotic, eucaryotic or viral DNA polymerases, and such a polymerase is used.

6. The method of claim 5, in which $Mg^{2+}$ is also included in the solution.

7. A method of claim 5, in which the correct nucleotide is labeled with [$\alpha$-$^{32}$P] of low specific activity and the incorrect nucleotide is labeled with [$^3$H] of high specific activity.

8. The method of testing in vitro a substance for the likelihood of mutagenic and carcinogenic properties, which comprises relicating a polynucleotide with a DNA polymerase in a solution containing a correct complementary and an incorrect non-complementary nucleotide for said polynucleotide in the absence of said substance, also replicating that polynucleotide by that same polymerase in a solution containing that substance, and comparing the results from the standpoint of production of mutations.

9. The method of testing a particular substance for likelihood of mutagenicity or carcinogenicity which comprises (a) synthesizing in vitro a particular polynucleotide which contains a particular first nucleotide and does not contain a particular second nucleotide, in a solution which contains as a template the same polynucleotide as is being synthesized and includes also the first nucleotide, the second nucleotide, a particular polymerase and the particular substance to be tested; also (b) synthesizing in vitro the same particular polynucleotide in a solution which contains as a template the same polynucleotide and includes also the first nucleotide, the second nucleotide and the same polymerase but does not include the particular substance to be tested; and (c) determining whether or not the proportion of second nucleotide to first nucleotide in the product of synthesis (a) significantly exceeds that in the product of synthesis (b).

* * * * *

UNITED STATES PATENT OFFICE
CERTIFICATE OF CORRECTION

Patent No. 4,072,574            Dated February 7, 1978

Inventor(s) Lawrence A. Loeb et al.

It is certified that error appears in the above-identified patent and that said Letters Patent are hereby corrected as shown below:

Column 1, line 34 "chemical" should read --- chemicals ---.

Column 4, line 25, "$32^P$" should read --- $32_P$ ---.

Column 7, line 37, "DCl" should read --- KCl ---.

Signed and Sealed this

Tenth Day of October 1978

[SEAL]

Attest:

RUTH C. MASON
*Attesting Officer*

DONALD W. BANNER
*Commissioner of Patents and Trademarks*